United States Patent [19]

Fischer, Jr.

[11] Patent Number: 5,052,386
[45] Date of Patent: Oct. 1, 1991

[54] METHOD AND APPARATUS FOR REPLACING A PLACED ENDOTRACHEAL TUBE

[75] Inventor: Frank J. Fischer, Jr., Bloomington, Ind.

[73] Assignee: Cook, Inc., Bloomington, Ind.

[21] Appl. No.: 420,550

[22] Filed: Oct. 12, 1989

[51] Int. Cl.$^5$ ............................................ A61M 16/04
[52] U.S. Cl. ............................ 128/207.15; 128/220.26; 128/912; 285/322
[58] Field of Search ..................... 128/207.15, 207.14, 128/200.26, 911, 912, DIG. 26, 207.16; 285/322, 323

[56] References Cited

U.S. PATENT DOCUMENTS

| 3,039,469 | 6/1962 | Fountain | 128/200.26 |
| 3,653,689 | 4/1972 | Sapy et al. | 285/322 |
| 3,948,273 | 4/1976 | Sanders | 128/207.15 |
| 4,231,365 | 11/1980 | Scarberry | 128/207.15 |
| 4,275,907 | 6/1981 | Hunt | 285/323 |
| 4,327,720 | 5/1982 | Bronson et al. | 128/207.15 |
| 4,328,983 | 5/1982 | Gibson | 285/382 |
| 4,329,987 | 5/1982 | Rogers et al. | 285/322 |
| 4,334,534 | 6/1982 | Ozaki | 128/207.15 |
| 4,398,757 | 8/1983 | Floyd et al. | 285/322 |
| 4,716,896 | 1/1988 | Ackerman | 128/200.26 |
| 4,819,664 | 4/1989 | Nazari | 128/207.15 |
| 4,846,167 | 7/1989 | Tibbals | 128/912 |
| 4,865,586 | 9/1989 | Hedberg | 128/207.14 |
| 4,892,095 | 1/1990 | Nakbgevany | 128/207.14 |
| 4,960,122 | 10/1990 | Mizus | 128/207.14 |

FOREIGN PATENT DOCUMENTS 445218 4/1936 United Kingdom ........... 128/200.26

OTHER PUBLICATIONS

"Mettro Mizus Endotracheal Tube Replacement Obturator Cook® Critical Care", Cook Incorporated, 1988.

Primary Examiner—Edgar S. Burr
Assistant Examiner—Stephen R. Funk
Attorney, Agent, or Firm—Richard J. Godlewski

[57] ABSTRACT

Method and apparatus are disclosed for replacing an endotracheal tube. The apparatus comprises an endotracheal tube obturator having an air passageway therein and a removable connector positioned at the proximal end of the obturator tube for ventilating the patient during replacement of the endotracheal tube. The obturator tube also includes a plurality of side ports for further ventilating the patient should mucous block the distal end of the obturator tube passageway. The removable connector includes a ventilator fitting and a removable and lockable obturator tube fitting joined thereto. The obturator tube fitting includes a sleeve having a plurality of flexible members for grasping the proximal end of the obturator tube. Extending into the passageway of the sleeve is a projection from the members for engaging the outside surface of the obturator tube when inserted in the passageway. A collar is slideably positionable about the sleeve between two retaining flanges for engaging a cam surface positioned on the flexible members for forcing the projections into the outside surface of the obturator tube. The apparatus is inserted into a placed endotracheal tube for ventilating the patient while the endotracheal tube is replaced. The quick removal connector permits the timely replacement of the endotracheal tube while maintaining ventilation of the patient.

23 Claims, 3 Drawing Sheets

METHOD AND APPARATUS FOR REPLACING A PLACED ENDOTRACHEAL TUBE

TECHNICAL FIELD

This invention relates to medical devices and particularly to method and apparatus for replacing a placed endotracheal tube.

BACKGROUND OF THE INVENTION

Presently, the replacement of an endotracheal tube placed in a patient includes disconnecting the endotracheal tube from a ventilator and inserting a sealed endotracheal obturator into the airway of the tube. The obturator is passed completely through the endotracheal tube and into the trachea of the patient. The endotracheal tube is then removed from the trachea of the patient over the obturator while the obturator remains in the trachea of the patient. Since the tissue surrounding a chronically placed endotracheal tube often becomes inflamed, an obturator is positioned in the passageway of the endotracheal tube to provide a guide for inserting the replacement tube through the inflamed tissue of the patient's airway. Furthermore, the patient's airway tissue may have become so inflamed as to completely encapsulate the obturator and essentially cut off air flow to the lungs. In many cases, the replacement endotracheal tube is simply inserted over the positioned obturator and quickly inserted into the patient's airway. As a result, ventilation of the patient is restored without any adverse affect to the patient. The obturator is withdrawn from the replacement endotracheal tube, and the replacement endotracheal tube is connected to the ventilation apparatus to resume normal ventilation of the patient.

However, during this replacement procedure, it is not uncommon to encounter problems in the insertion of the replacement endotracheal tube. The tissue of the patient's airway passage may have become so inflamed so as to make the insertion of the replacement endotracheal tube a time-consuming process even with the obturator positioned in the patient. The insertion of the replacement endotracheal tube may also cause trauma or bleeding to the airway passage tissue further complicating the replacement process. The physician can readily accommodate these complications; however, time becomes a critical factor when the inflamed tissue has entirely blocked the airway preventing normal ventilation of the patient.

Instead of a sealed obturator, physicians have been known to cut off a length of medical grade tubing with an airway therein to serve as an endotracheal tube obturator. In those instances where the physician is aware of the severely inflamed tissue condition, this tube provides limited ventilation of the patient during the replacement procedure. However, the cut-off tube does not have any fitting or connector for connection to ventilating equipment during the replacement procedure. Furthermore, the distal end of this makeshift obturator often becomes blocked with mucous as the tube extends beyond the distal end of the endotracheal tube. Such blockage is commonly unknown to the physician until the endotracheal tube is removed. As a result, the makeshift obturator does not alleviate the ventilation problem during a prolonged replacement procedure and, in fact, prolongs the procedure due to it being more flexible than most endotracheal obturators.

SUMMARY OF THE INVENTION

The foregoing problems are solved and a technical advance is achieved with illustrative method and apparatus for replacing an endotracheal tube placed in a patient. The apparatus includes an obturator tube having an airway therein, which is insertable into the passageway of the endotracheal tube for ventilating the patient during replacement. Furthermore, the apparatus includes a removable connector positioned about the proximal end of the obturator tube for connection to a ventilator. This removable connector also has a lock mechanism for ensuring continued connection with the obturator tube. As a result, this replacement apparatus advantageously provides a positive means of ventilating the patient during replacement of the placed endotracheal tube.

Illustratively, the method for replacing a placed endotracheal tube while maintaining ventilation of the patient includes disconnecting the placed endotracheal tube from the ventilator apparatus and connecting the obturator tube to the ventilator apparatus. The connection of the obturator tube includes the use of the removable connector which includes a standard ventilator fitting. The method further includes inserting the obturator tube into the placed endotracheal tube and removing the placed endotracheal tube from the patient over the obturator tube. The obturator tube is disconnected from the ventilator apparatus and the endotracheal removed from about the obturator tube. The disconnection step is facilitated by the use of the removable connector which is unlocked and removed from the proximal end of the obturator tube to permit removal of the removed endotracheal tube over the obturator tube. The replacement endotracheal tube is then inserted over the obturator tube with the obturator tube being reconnected to the ventilator apparatus utilizing the removable and lockable connector. The obturator tube and removable connector advantageously minimize the time period in which the ventilator apparatus is not providing positive ventilation of the patient. With the obturator tube providing ventilation of the patient during removal of the endotracheal tube and the insertion of the replacement, the physician has ample time for placing the replacement tube with minimal, if any, trauma to the already inflamed tissue of the patient's airway. After the replacement endotracheal tube is placed, the obturator tube is removed and disconnected from the ventilator apparatus. The ventilator apparatus is then reconnected to the patient.

The obturator tube of the replacement apparatus also includes one or more indicators positioned a predetermined distance from the distal end of the tube for indicating the position of the obturator tube in the placed endotracheal tube. In the illustrative embodiment, these indicators include a radiopaque substance which is painted on the outside of the obturator tube. This advantageously provides the physician with a visual indication of the depth of penetration of the obturator tube in the patient. Furthermore, the radiopaque indicator provides X-ray or other aided visualization of the obturator tube in the patient.

Should the distal end of the obturator tube become blocked with patient mucous, the obturator tube advantageously includes a plurality of side ports positioned about the distal end of the tube for further ventilating the patient during replacement of the endotracheal tube.

A significant departure in the art includes the use of the removable and lockable connector of the replacement apparatus for connecting the obturator tube to ventilator apparatus. Illustratively, the connector includes a ventilator tube fitting and an obturator tube fitting ultrasonically joined together. The obturator tube fitting includes a sleeve having a passageway for receiving the proximal end of the obturator tube. The sleeve is slotted from the distal end to form a plurality of radially flexible members for grasping the proximal end of the obturator tube. A ridge or projection extending radially and inwardly into the sleeve passageway grasps the preferably semi-rigid material of the obturator tube. This fixedly positions the tube longitudinally in the connector. The obturator tube fitting also includes a ring-like collar positioned about the sleeve and engageable with the radially flexible members for moving the flexible members and the projection thereon into the surface of the obturator tube. The flexible members include a cam surface at the distal end thereof for engaging the ring-like collar. To unlock the fitting to provide easy disengagement of the locking collar, the surface adjacent the cam surface is recessed below the cam surface to limit the amount of engagement of the collar with the cam surface.

To provide an airtight seal, the connector of the replacement apparatus includes an O-ring seal positioned at the proximal end of the obturator tube fitting for pneumatically sealing the obturator tube in the sleeve passageway.

BRIEF DESCRIPTION OF THE DRAWINGS

FIG. depicts illustrative endotracheal tube replacement apparatus of the present invention for removing an endotracheal tube placed in a patient.

DETAILED DESCRIPTION

Figure 1:
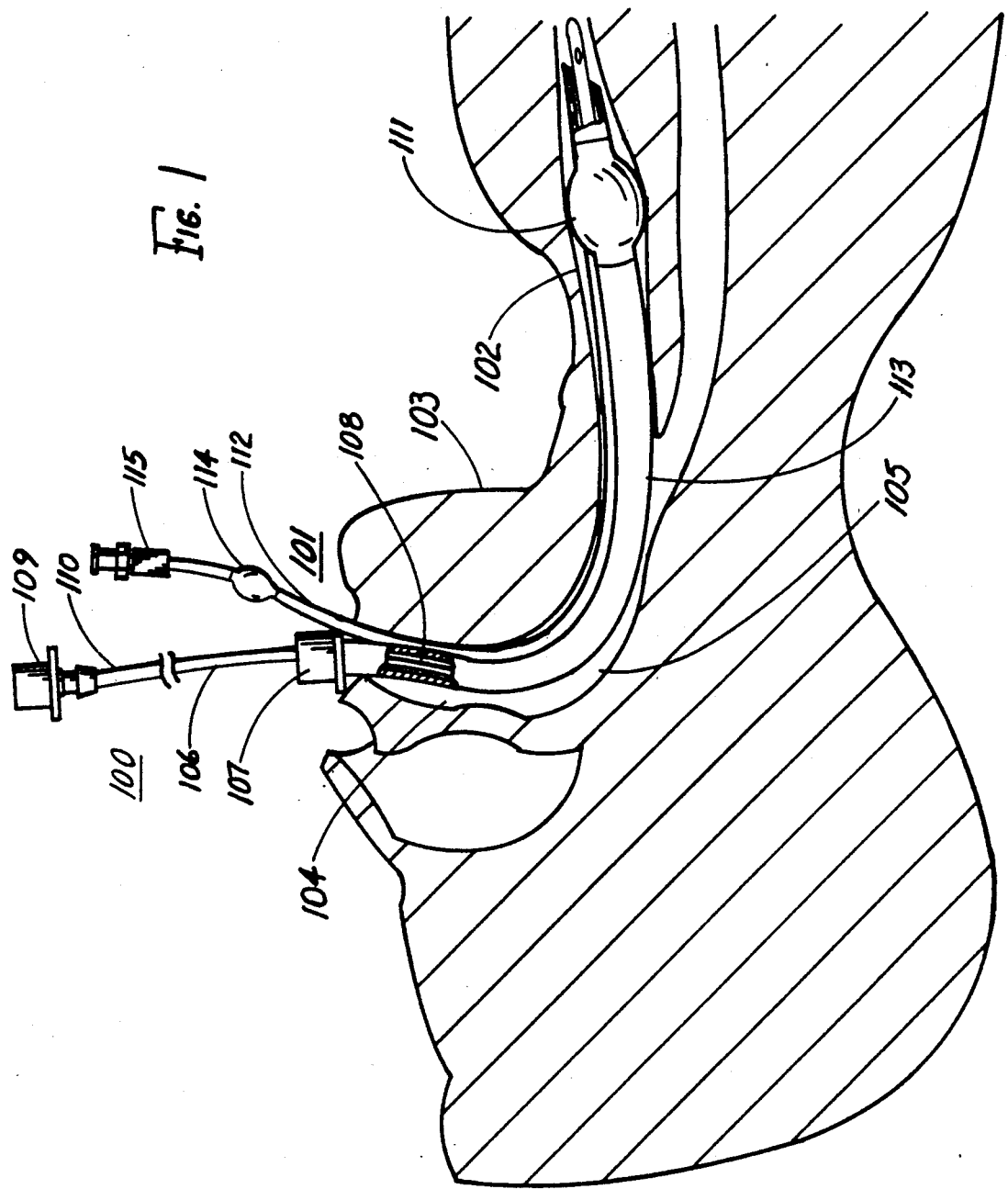

Depicted in FIG. 1 is illustrative endotracheal tube replacement apparatus 100 for replacing an endotracheal tube 101 placed in trachea 102 of patient 103. The endotracheal tube is a well-known medical device and is placed through mouth 104 and airway 105 and into the trachea of the patient. The endotracheal tube replacement apparatus includes an obturator tube 106 which is inserted through ventilator connector 107 and ventilating passageway 108 of the endotracheal tube and into the trachea of the patient. The replacement apparatus also includes a removable connector 109 positioned about proximal end 110 of the obturator tube for ventilating the patient during replacement of the endotracheal tube. Endotracheal tube 101 is a well-known medical device and typically includes an inflatable cuff 111 positioned at the distal end thereof for securely positioning and sealing the distal end of the endotracheal tube in the trachea. This cuff is inflatable with air supplied through an inflation tube 112 attached to the external surface of endotracheal tube 113. An inflatable balloon 114 and an airtight connector 115 are positioned at the proximal end of the inflation tube for inflating the cuff and for providing a visual indication of the inflation of the cuff.

The method for replacing endotracheal tube 101 placed in patient 103 while maintaining ventilation thereof, comprises disconnecting the endotracheal tube from ventilator apparatus (not shown) at endotracheal tube ventilator connector 107 and connecting the ventilator apparatus to endotracheal tube replacement apparatus 100 via removable ventilator connector 109. The obturator tube is inserted through ventilator connector 107 and passageway 108 of the endotracheal tube beyond the distal end thereof and into the trachea 102 of the patient. When inserted as shown and connected to the ventilator apparatus, positive ventilation of the patient is maintained. The endotracheal tube is then removed from the trachea and airway of the patient over the obturator tube while the obturator tube remains placed in the trachea of the patient. With a chronically placed endotracheal tube, it is common for the tissue of the patient's airway to become inflamed thereby encapsulating the endotracheal tube. When the endotracheal tube is removed, the inflamed tissue commonly encapsulates the obturator tube, thereby preventing the passage of air through the patient's airway around the obturator tube. Since the obturator tube includes a passageway therein, ventilation of the patient is maintained even though the inflamed tissue encapsulates the obturator tube.

When the endotracheal tube is removed from the passageway of the patient over the obturator tube, removable connector 109 is removed from obturator tube 106, thereby disconnecting the obturator tube from the ventilator apparatus. The removed endotracheal tube is then completely removed from the patient over the obturator tube and a replacement endotracheal tube is inserted over the obturator tube. The removable connector is reconnected and locked to the proximal end of the obturator tube, thereby reconnecting the ventilator apparatus to the obturator tube for providing continued ventilation of the patient. When the ventilator apparatus is reconnected to the obturator tube, the physician is permitted ample time to place the replacement endotracheal tube in the trachea of the patient without causing trauma to the surrounding inflamed tissue of the airway. After the physician places the replacement endotracheal tube in the airway and trachea of the patient, the obturator tube is removed from the ventilating passageway of the endotracheal tube and disconnected from the ventilator apparatus. The ventilator apparatus is then connected to the endotracheal tube placed in the patient.

Figure 2:
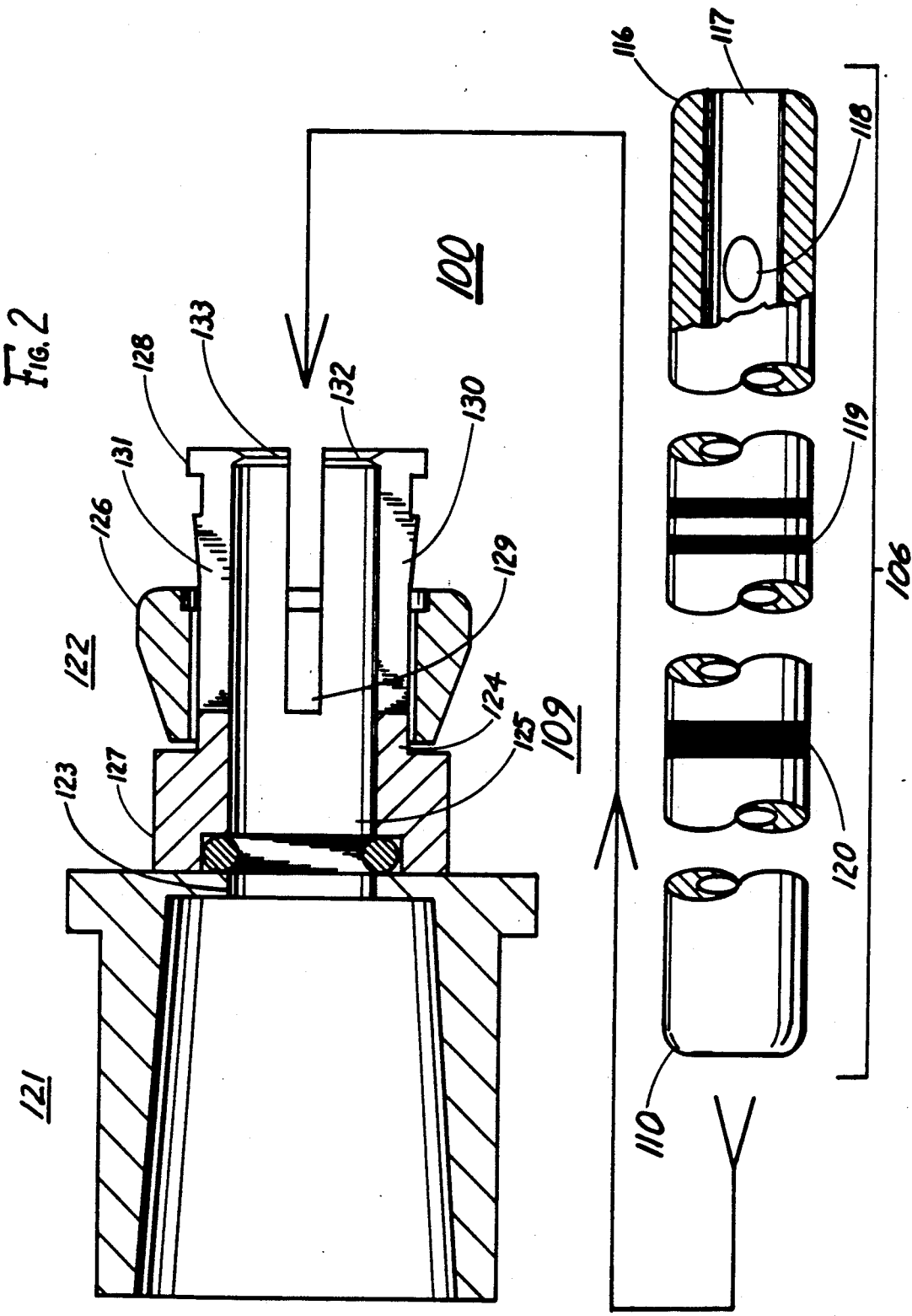
FIG. 2 depicts a partially sectioned and more detailed drawing of the replacement apparatus of the invention depicted in FIG. 1.

Depicted in FIG. 2 is a more detailed and partially sectioned view of endotracheal tube replacement apparatus 100. As shown, replacement apparatus 100 basically comprises obturator tube 106 and removable and lockable connector 109. Obturator tube 106 is preferably of a semi-rigid material such as radiopaque polyethylene and includes proximal end 110 and distal end 116 with air passageway 117 therebetween. The outside diameter of this semi-rigid obturator tube is typically 18 French for inserting through standard ventilator connectors such as 107 and into passageway 108 of endotracheal tube 113. The inside diameter of the obturator tube is 0.115". A plurality of side ports such as port 118 is positioned approximately 1" from distal end 116 for providing further ventilation of the patient. Side ports are elliptical or oval in shape for providing the largest area port without significantly weakening the structure of the tube. The side ports provide ventilation of the patient should mucous enter passageway 117 at the distal end. The obturator tube is typically 70 cm in length with a plurality of indicators such as 119 and 120 positioned approximately 13 and 40 cm from the distal end thereof. The length of the tube is somewhat more than twice the length of the endotracheal tube to permit handling thereof during the replacement procedure. These indicators are formed on the outer surface of the tube with, for example, commercially-available Markem ink which is a radiopaque ink distinguishable from the radiopaque obturator tube material. The physician visually observes these indicators during the insertion of the tube into the endotracheal tube for indicating relative positioning of the obturator tube in the patient. Further verification of the positioning of the obturator tube in the patient is provided with the radiopaque property of the tube and indicators visualized with the use of, for example, X-ray equipment. The distal end 116 of the tube is rounded for minimizing trauma to the trachea of the patient. In a similar manner, proximal end 110 is rounded to provide an airtight or pneumatic seal with connector 109 when inserted therein.

As depicted in FIG. 2, removable connector 109 includes a well-known ventilator fitting 121 and obturator tube fitting 122 that are joined together. As illustrated, ventilator fitting 121 is preferably of a plastic material such as polycarbonate which is available from Bivona, Inc. of Gary, Ind. The ventilator fitting is available as part No. CO-30 from Bivona with a male nipple (not shown) for insertion into a ventilator tube. The ventilator fitting is modified by removing the nipple and increasing distal opening 123 to approximately 0.250".

The removable and lockable obturator tube fitting 122 of the present invention is also preferably of a plastic material such as polycarbonate which is ultrasonically welded to the distal end of ventilator fitting 121. The obturator tube fitting 122 comprises a slotted sleeve 124 having a passageway 125 and a ring-like collar 126 positioned thereabout between radially extending flanges 127 and 128 at the respective ends of the sleeve.

Sleeve 124 has a plurality of slots such as 129 formed from the distal end. The slotting of the sleeve produces a plurality of flexible members 130 and 131, which are radially flexible at the distal end. When proximal end 110 of the obturator tube is inserted in passageway 125, the flexible members move in a radially outward direction. Each flexible member includes a projection or ridge such as 132 and 133 extending into passageway 125. The dimension between the peaks of opposing projections of the flexible members is less than the outside diameter of the obturator tube. As a result, when the obturator tube is inserted in passageway 125, the distal end of the flexible members are moved in an outward direction due to the surface of the obturator tube engaging the projections.

Figure 3:
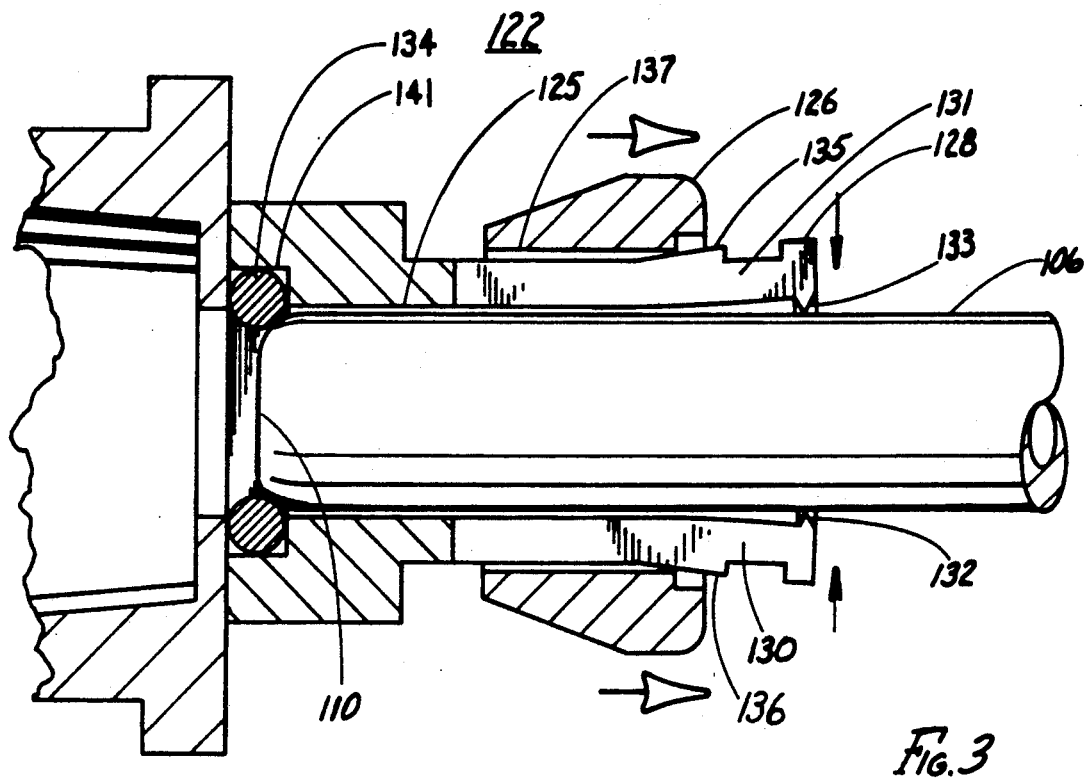
FIG. 3 depicts the obturator tube of FIGS. 1 and 2 fully inserted in the removable connector of the present invention with a locking collar partially engaged.

Depicted in FIG. 3 is a partially sectioned view of the replacement apparatus of FIG. 2 with the proximal end 110 of the obturator tube fully inserted into passageway 125 of obturator tube fitting 122. As shown, the proximal end of the obturator tube engages O-ring seal 134 positioned at the proximal end of the obturator tube fitting. The O-ring seal is positioned in recess 141 at the proximal end of the obturator tube fitting. This O-ring seal is made preferably of commercially available Buna-N rubber. When the proximal end of the tube is positioned next to the O-ring seal, obturator tube 106 is pneumatically sealed in fitting passageway 125. As also shown, the proximal end 110 of the obturator tube flexes the distal end of the members in an outward direction due to the projections engaging the outside surface of the obturator tube.

Cylindrically shaped flexible members 130 and 131 have a conically shaped cam surface 135 and 136 at their distal ends. The inside surface 137 of ring-like collar 126 engages these cam surfaces when the collar is moved toward the distal end of the members as shown. When the inside surface of the collar engages the cam surfaces, projections 132 and 133 are forced in an inward direction indicated by the arrows and into the outside surface of semi-rigid material obturator tube 106.

Figure 4:
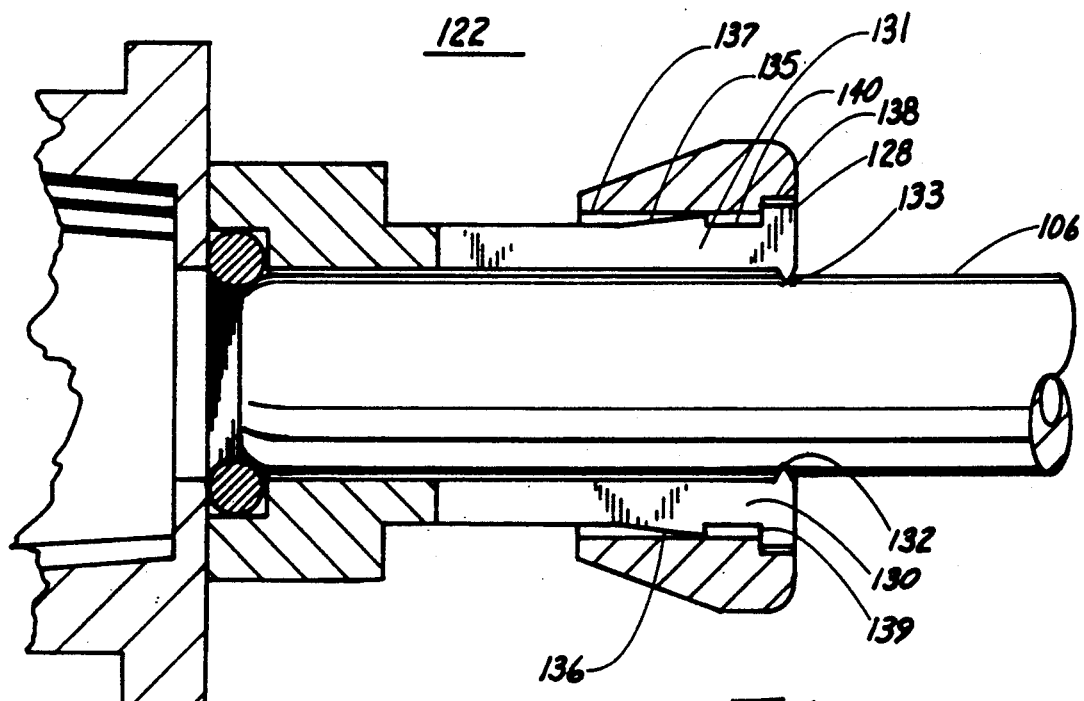
FIG. 4 depicts the obturator tube fully inserted in the removable connector in a fully locked position.

As depicted in FIG. 4, collar 126 has been moved to a fully distal position to engage retainer flange 128 at the distal end of the members. The inside of the collar is cut to form a notch 138 to engage retaining flange 128. When moved to a fully distal position, surface 137 of the collar fully engages the cam surfaces forcing projections 132 and 133 fully into the outside surface of obturator tube 106. As a result, the flexible members and projections fixedly position longitudinally the proximal end of the obturator tube in the fitting passageway.

When collar 126 has been extended to a full distal position engaging retaining flange 128, the removable connector is in a "locked position." To unlock the removable connector, collar 126 is slid by the physician to the proximal position disengaging cam surface 135 and 136 of flexible members 130 and 131, respectively. The flexible members include a recessed surface or notch 139 and 140 of respective flexible members 130 and 131. These recessed surfaces adjacent cam surfaces 135 and 136 limit the engagement of the collar with the flexible members. As a result, the force necessary to move the collar to a proximal position is significantly reduced. However, sufficient force is exerted by the semi-rigid tube against the projections and flexible members to maintain the connector in a "locked" position.

Although the removable connector has been described for interconnecting an obturator tube to ventilator apparatus, this removable connector may be used for any number of applications for interconnecting two tubes for which quick-release is desired.

Of course, it will be understood that the aforementioned endotracheal tube replacement apparatus and method is merely illustrative of the application of the principles of this invention and that numerous other arrangements may be devised by those skilled in the art without departing from the spirit and scope of the invention. In particular, the projections extending from the flexible members may be positioned elsewhere along the length of the sleeve passageway. This provides additional force if required depending on the durometer of the semi-rigid material. The depth or the height of the projections may also be increased to further extend into a softer material tube. In addition, any number of different connector fittings may be ultrasonically welded or joined to the lockable and removable fitting of the present invention.

What is claimed is:

1. Apparatus for replacing an endotracheal tube placed in a patient, comprising:
    tubular obturator means for ventilating said patient during replacement of said endotracheal tube, said obturator means being insertable into a passageway of said endotracheal tube and having distal and proximal ends, a passageway extending therethrough, an outside surface extending longitudinally therealong, and said outside surface of said obturator means being passable throughout the entire length of said passageway of said endotracheal tube so that the entirety of said obturator means may pass through said passageway of said endotracheal tube; and removable connector means positioned about said proximal end and fixedly engaged with said outside surface of said tubular obturator means for engaging said outside surface and connecting said tubular obturator means to a ventilator.

2. The apparatus of claim 1 wherein said tubular obturator means includes indicator means positioned a predetermined distance from said distal end for indicating the position of said tubular obturator means in said endotracheal tube.

3. The apparatus of claim 1 wherein said tubular obturator means includes side port means positioned about said distal end for further ventilating said patient during replacement of said endotracheal tube.

4. The apparatus of claim 1 wherein said removable connector means includes sleeve means having a passageway for receiving said proximal end of said tubular obturator means.

5. The apparatus of claim 4 wherein said sleeve means includes radially flexible means for grasping said outside surface about said proximal end of said tubular obturator means.

6. The apparatus of claim 5 wherein said radially flexible means includes said projection means extending into said sleeve passageway for fixedly and longitudinally positioning said proximal end of said tubular obturator means in said sleeve passageway.

7. The apparatus of claim 5 wherein said removable connector means includes collar means engageable with said radially flexible means for fixedly and radially positioning said radially flexible means when said tubular obturator means is in said sleeve passageway.

8. The apparatus of claim 7 wherein said radially flexible means includes means for limiting engagement of said collar means with said radially flexible means.

9. The apparatus of claim 4 wherein said removable connector means includes seal means for pneumatically sealing said tubular obturator means in said sleeve passageway.

10. The apparatus of claim 1 wherein said removable connector means includes lock means for fixedly positioning said removable connector means about said proximal end of said tubular obturator means.

11. An endotracheal tube obturator comprising:

a semi-rigid tube insertable into a passageway of an endotracheal tube, said semi-rigid tube having distal and proximal ends, a passageway extending therethrough, an outside surface extending longitudinally therealong, said outside surface of said semi-rigid tube being passable throughout the entire length of said passageway of said endotracheal tube so that the entirety of said semi-rigid tube may pass through said passageway of said endotracheal tube, and a plurality of side ports positioned about said distal end; and a removable ventilator connector positioned about said proximal end and fixedly engageable with said outside surface of said semi-rigid tube.

12. The obturator of claim 11 wherein said semi-rigid tube has a radiopaque indicator positioned a predetermined distance from said distal end.

13. The obturator of claim 11 wherein said removable ventilator connector includes a ventilator fitting and a tube fitting joined together.

14. The obturator of claim 13 wherein said removable ventilator connector includes an O-ring seal.

15. The obturator of claim 13 wherein said tube fitting comprises a sleeve having a passageway for said proximal end of said semi-rigid tube.

16. The obturator of claim 15 wherein said sleeve further comprises a plurality of radially flexible members, said members grasping said outside surface of said proximal end of said semi-rigid tube when positioned in said sleeve passageway.

17. The obturator of claim 16 wherein said radially flexible members include a projection extending into said sleeve passageway and forced into said outside surface of said semi-rigid tube.

18. The obturator of claim 17 wherein said radially flexible members include a conically-shaped cam surface and wherein said tube fitting further comprises a collar longitudinally positionable about said sleeve and engageable with said conically-shaped cam surface, when engaged with said flexible members said collar forcing said projection into said outside surface of said semi-rigid tube when inserted in said sleeve passageway.

19. The obturator of claim 18 wherein said radially flexible members include a recessed surface adjacent said conically-shaped cam surface, said recessed surface limiting engagement of said collar with said radially flexible members.

20. The obturator of claim 17 wherein said tube fitting comprises a colar positioned around and engageable with said radially flexible members, when engaged with said members said collar forcing said projection into said outside surface of said semi-rigid tube when inserted in said sleeve passageway.

21. Method for replacing an endotracheal tube placed in a patient while maintaining ventilation thereof, comprising:

disconnecting said endotracheal tube from ventilator apparatus;

connecting an endotracheal obturator tube having a passageway therein to said ventilator apparatus;

inserting said obturator tube in said endotracheal tube;

removing said endotracheal tube from said patient over said obturator tube;

disconnecting said obturator tube from said ventilator apparatus;

removing said endotracheal tube from about said obturator tube;

inserting a replacement endotracheal tube over said obturator tube;

reconnecting said obturator tube to said ventilator apparatus;

placing said replacement endotracheal tube in said patient;

removing said obturator tube;

disconnecting said obturator tube from said ventilator apparatus; and connecting said ventilator apparatus to said replacement endotracheal tube placed in said patient.

22. The method of claim 21 wherein the step of disconnecting said obturator tube from said ventilator apparatus includes disconnecting a removable connector interconnecting said ventilator apparatus and said obturator tube, from said obturator tube.

23. The method of claim 22 wherein the step of reconnecting said obturator tube to said ventilator apparatus includes reconnecting said removable connector to said obturator tube.

* * * * *